United States Patent [19]
Taub et al.

[11] 3,939,152
[45] Feb. 17, 1976

[54] 5-PHENYL-2,4-BENZODIAZEPINES

[75] Inventors: William Taub, Harishom; Uri Golik, Givataym, both of Israel

[73] Assignee: Yeda Research and Development Company Ltd., Israel

[22] Filed: Mar. 29, 1974

[21] Appl. No.: 456,015

[30] Foreign Application Priority Data
Apr. 4, 1973 United Kingdom............... 16109/73

[52] U.S. Cl. .... 260/239.3 B; 424/244; 260/239.3 T; 260/558 R
[51] Int. Cl.² ...................................... C07D 243/00

[58] Field of Search .............................. 260/239.3 B

[56] References Cited
UNITED STATES PATENTS
3,293,243   12/1966   Sulkowski .................... 260/239.3 B Primary Examiner—Robert T. Bond

[57] ABSTRACT

5-Phenyl-2,4-benzodiazepines useful as psychotropic agents and their pharmaceutically acceptable salts and N-oxides, procedure for their production and oral dosage unit pharmaceutical compositions containing said agents.

10 Claims, No Drawings

5-PHENYL-2,4-BENZODIAZEPINES

This invention relates to novel 5-phenyl-2,4-benzodiazepines which have pharmacologically useful properties as psychotropic agents, to a process for their preparation and to compositions containing them.

Accordingly, the present invention provides compounds of formula (I):

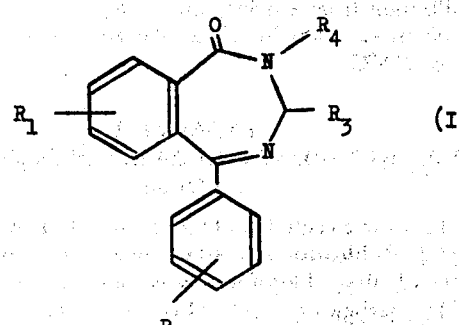

(I)

and salts and N-oxides thereof wherein $R_1$ is a hydrogen or halogen atom or a nitro, methyl, cyano or trifluoromethyl group; $R_2$ is a hydrogen or halogen atom or a nitro, methyl, cyano or trifluoromethyl group; $R_3$ is a hydrogen atom or methyl group; $R_4$ is a hydrogen atom or a methyl or ethyl group; and salts and N-oxides thereof.

Most suitable compounds of formula (I) include those wherein $R_1$ and $R_2$ are each a hydrogen or halogen atom or a nitro or trifluoromethyl group; $R_3$ is hydrogen or methyl and $R_4$ is hydrogen or methyl. Most suitably $R_1$ is in the 7- position.

Preferred compounds of formula (I) include those wherein $R_3$ and $R_4$ are both hydrogen atoms; $R_1$ is a fluorine, chlorine, nitro or trifluoromethyl group; and $R_2$ is a hydrogen atom. Compounds of formula (I) include:

5-Phenyl-2,3-dihydro-1H-2,4-benzodiazepine-1-one
5-Phenyl-2,3-dihydro-1H-2,4-(7-chlorobenzodiazepine)-1-one
5-Phenyl-2,3-dihydro-1H-2,4-(7-nitrobenzodiazepine)-1-one
5-Phenyl-2,3-dihydro-1H-2-methyl-2,4-benzodiazepine-1-one
5-(3-Chlorophenyl)-2,3-dihydro-1H-2,4-benzodiazepine-1-one
5-Phenyl-2,3-dihydro-1H-2,4-benzodiazepine-1-one-4-oxide
5-Phenyl-2,3-dihydro-1H-2,4-(7-nitrobenzodiazepine)-1-one-4-oxide This invention also provides pharmaceutical compositions comprising a compound of formula (I) together with a pharmaceutically acceptable carrier. Such compositions may be in unit dosage forms such as tablets, capsules, sachets or premeasured doses to make up into injectable forms in standard manner.

Generally, unit dosage forms will contain from 2–100 mgs. of a compound of formula (I) and will normally contain from 10–50 mgs. of such a compound.

The compounds of formula (I) may be prepared by the cyclisation of a compound of formula (IIa)

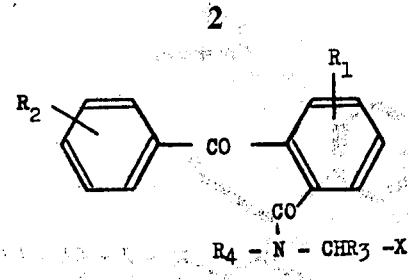

(IIa, X = NH$_2$);
(IIb, X = Cl, Br, etc).

and thereafter if desired, oxidizing the benzodiazepine so formed in order to produce the N-oxide in conventional manner.

As compounds of the formula (IIa) tend to be unstable because of their ability to cyclise they are preferably formed in situ from the corresponding compound of formula (IIb) in which X is a halogen, pseudo halogen or other common readily displaceable group (preferably a chlorine or bromine group) by reaction with ammonia. This reaction normally takes place in a hydroxylic solvent and the benzodiazepine may be obtained by treating a compound of formula (IIb) with an excess of aqueous ammonia.

The oxidation of the benzodiazepines to their N-oxides is preferably brought about by the action of a per-acid in conventional manner. This reaction may be preformed with advantage in an organic solvent such as chloroform.

A side product of the oxidation reaction frequently results and has been shown to be of the structure (III):

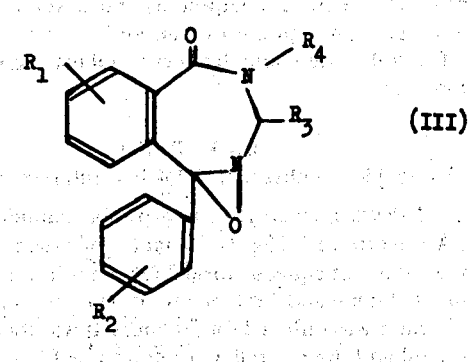

(III)

Such compounds are isolatable from the reaction mixture by chromatography.

The compounds of formula (III) also form an aspect of this invention as they have some CNS activity.

The intermediates (IIb) may be prepared according to the following scheme:

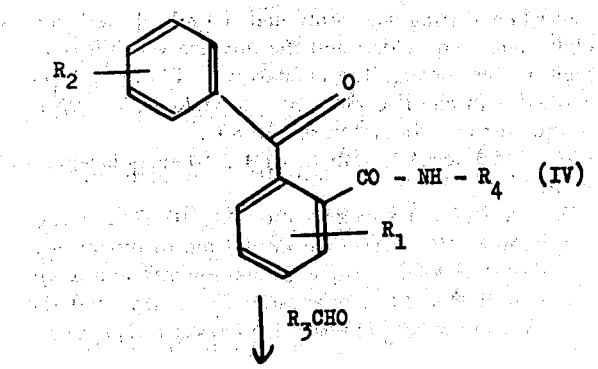

(IV)

—Continued

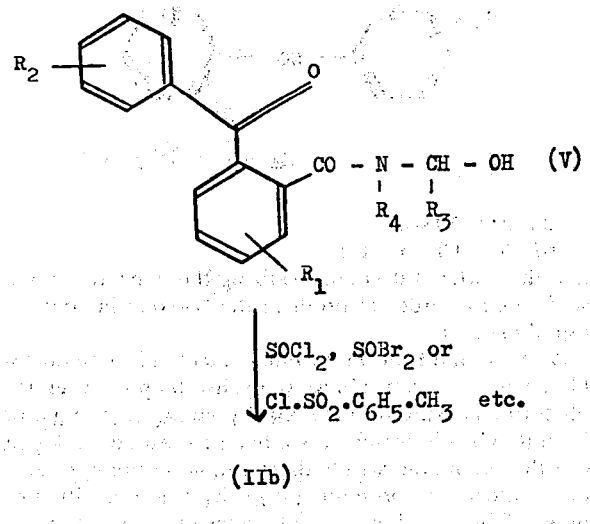

(IIb)

The reaction between the benzamide of formula (IV) and the aldehyde R₃CHO may take place in an aqueous basic solution. The reaction is generally fairly slow and often requires heating to reflux for a long period for example, 15-36 hours. Reactions with acetaldehyde are less easy than those with formaldehyde.

The production of a compound of formula (IIb) from the alcohol occurs in (V) under conventional conditions.

It is believed that the valuable intermediates of formula (II) are novel compounds and as such, they form an aspect of the present invention.

The following Examples serve to illustrate the invention:

EXAMPLE 1
5-Phenyl-2,3-dihydro-1H-2,4-benzodiazepine-1-one a. N-Hydroxymethyl-(2-benzoyl)benzamide A mixture of 2.25g. (0.01 mole) of o-benzoylbenzamide, 4 ml. of aqueous formaldehyde solution (38%), 4 ml. of ethanol and 4 ml. of a solution of 1g. $K_2CO_3$ in 35 ml. water was refluxed for 20 hours. It was then allowed to cool and the crystalline product was filtered off and washed with water to yield 2.2g. (85%) of analytically pure material, m.p. 166/8°C.

b. N-Chloromethyl-(2-benzoyl)benzamide

To 1g. (0.004 mole) of the benzamide 0.5 ml. of thionyl chloride was added drop-wise while external cooling and stirring were applied. The crystalline starting material turned into a yellowish oil, which resolidified when stirring was continued. 10 ml. of methylcyclohexane were added and the mixture was left overnight under stirring. The crystals were filtered off and washed with methylcyclohexane to yield 1.05g. (95%) of the desired product, m.p. 136/8°C.

c. 5-Phenyl-2,3-dihydro-1H-2,4-benzodiazepine-1-one

To a cooled and stirred solution 20g. (0.073 mole) of the chloromethyl derivative in 300 ml. of dioxan was added 400 ml. of 25% aqueous ammonia. The mixture was stirred at room temperature for 2 days and the solvents evaporated off under low pressure. The resulting oily residue was dissolved in ethyl acetate and washed with water. The organic layer was dried (MgSO₄) and the solvent then removed under reduced pressure. The resulting oil was taken up in a little chloroform and chromatographed on a silical gel column (200g. HF 254) using chloroform as eluant. The major quantities of product were in fractions 9, 10 and 11 (150 ml. per fraction). Evaporation of the solvent under reduced pressure yielded a solid which on recrystallization from ethylacetate, yielded 2.05g. (12%) of 5-phenyl-2,3-dihydro-1H-2,4-benzodiazepine-1-one. m.p. 215°C.

EXAMPLE 2
5-Phenyl-2,3-Dihydro-1H-2,4-Benzodiazepine-1-one-4-Oxide

To a stirred solution of 0.83g. (0.004 mole) of 5-phenyl-2, 3-dihydro-1H-2,4-benzodiazepine-1-one in 50 ml. of dry chloroform was added 0.85g. of m-chloroperbenzoic acid. After 20 hours of additional stirring at room temperature, the reaction mixture was successively washed with 20 ml. of a 5% potassium carbonate solution and water, dried over magnesium sulphate and evaporated to dryness at reduced pressure to leave a residue consisting of a yellowish oil. Chromatography over a silica gel (HF 254) column (30g.) yielded 0.1g. (10%) of the oxaziridine derivative (V; $R_1-R_6 = H$) using a mixture of equal parts of chloroform and benzene as eluant. This compound was isolated from fractions 8-9-10 (75 ml. per fraction), m.p. 180°C (ex. benzene). Further elution with chloroform was of no avail. On elution with ethyl acetate, the 0.4g. of the corresponding N-oxide was obtained (40%), m.p. 216/7°C. Recrystallization of the N-oxide from benzene yielded colourless crystals (which also contained 2 moles of benzene) of 5-phenyl-2,3-dihydro-1H-2,4-benzodiazepine-1-one-4-oxide, m.p. 102/3°C.

EXAMPLE 3.
5-Phenyl-2,3-dihydro-1H-2,4-(7-chlorobenzodiazepine)-1-one a. N-Hydroxymethyl-[2-(4.chloro)benzoyl]benzamide This compound was prepared in a manner exactly analogous to that described in Example 1a. The melting point of the compound was 214°C.

b. N-chloromethyl-[2-(4-chloro)benzoyl]benzamide

This compound was prepared in a manner exactly analogous to that described in Example 1b. but was not isolated instead used in situ.

c. 5-Phenyl-2,3-dihydro-1H-2,4-(7-chlorobenzodiazepine)-1-one

This compound was prepared in a manner exactly analogous to that described in Example 1c. The melting point of the compound was 139°C.

d. Pharmacology

The title compound was active on standard tests as follows:

Anti-metrazol Convulsions: $ED_{50}$ = 1.5mg/kg
Maximal Electro Shock: 40% effect at 25mg/kg
Irwin Profile: Depression at 25mg/kg

What we claim is:

1. A compound of the formula (I):

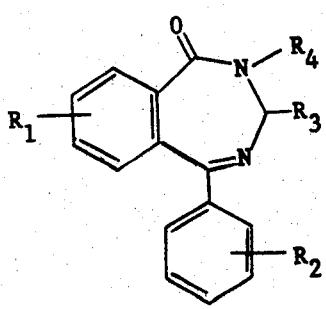

(I)

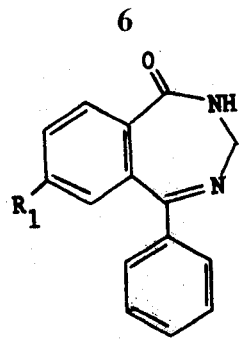

or a pharmaceutically acceptable salt or N-oxide thereof wherein R₁ is a hydrogen or halogen atom or a nitro, methyl, cyano or trifluoromethyl group; $R_2$ is a hydrogen or halogen atom or a nitro, methyl, cyano or trifluoromethyl group; $R_3$ is a hydrogen atom or a methyl group; $R_4$ is a hydrogen atom or a methyl or ethyl group.

2. A compound according to claim 1 wherein $R_1$ is a hydrogen or halogen atom or a nitro or trifluoromethyl group; $R_2$ is a hydrogen or halogen atom or a nitro or trifluoromethyl group; and $R_4$ is a hydrogen atom or methyl group.

3. A compound according to claim 2 wherein $R_1$ is in the 7-position.

4. A compound of the formula wherein $R_1$ is a fluorine, chlorine, nitro or trifluoromethyl group, or a pharmaceutically acceptable acid addition salt or N-oxide thereof.

5. 5-Phenyl-2,3-dihydro-1H-2,4-benzodiazepine-1-one or a pharmaceutically acceptable acid addition salt.

6. 5-Phenyl-2,3-dihydro-1H-2,4-benzodiazepine-1-one-4-oxide.

7. 5-Phenyl-2,3-dihydro-1H-2,4-(7-chlorobenzodiazepine)-1-one or a pharmaceutically acceptable acid addition salt.

8. 5-Phenyl-2,3-dihydro-1H-2,4-(7-chlorobenzodiazepine)-1-one-4-oxide.

9. 5-Phenyl-2,3-dihydro-1H-2,4-(7-nitrobenzodiazepine)-1-one or a pharmaceutically acceptable acid addition salt.

10. 5-Phenyl-2,3-dihydro-1H-2,4-(7-nitrobenzodiazepine)-1-one.

* * * * *